United States Patent [19]
Engler et al.

[11] Patent Number: 6,133,035
[45] Date of Patent: *Oct. 17, 2000

[54] METHOD OF GENETICALLY TRANSFORMING BANANA PLANTS

[75] Inventors: Dean Engler, Moraga; Neal Gutterson, Oakland, both of Calif.; Garry S. Nisbet, Woodley, United Kingdom

[73] Assignees: DNA Plant Technology Corporation, Oakland, Calif.; Zeneca, Ltd., London, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/895,334

[22] Filed: Jul. 16, 1997

[51] Int. Cl.⁷ .................... A01H 4/00; C12N 5/14
[52] U.S. Cl. .......... 435/419; 435/418; 435/410; 435/252.3; 435/320.1; 536/23.1; 536/23.2; 800/278; 800/279
[58] Field of Search .................. 800/278, 279, 800/294; 435/419, 418, 410, 252.3, 320.1; 536/23.1

[56] References Cited

U.S. PATENT DOCUMENTS

| | | |
|---|---|---|
| 5,231,019 | 7/1993 | Paszkowski et al. . |
| 5,424,412 | 6/1995 | Brown et al. . |
| 5,591,616 | 1/1997 | Hiei et al. ............. 435/172.3 |
| 5,689,046 | 11/1997 | Schroder et al. . |
| 5,716,837 | 2/1998 | Barry et al. . |

FOREIGN PATENT DOCUMENTS

WO95/15678  6/1995  WIPO ............. C12N 15/14

OTHER PUBLICATIONS

F.J. Novak, et al. "Somatic embryogenesis and plant regeneration in suspension cultures of dessert (AA and AAA) and cooking (ABB) bananas (*MUSA* SPP.)." BioTechnology, 7 (1989).

J. V. Escalant, et al. "Somatic embryogenesis and plants from immature zygotic embryos of the species *Musa acuminata* and *Musa balbisiana*." Plant Cell Reports (1989).

L. Sagi, et al. "Transient gene expression in electroporated banana (*musa spp., cv. "Bluggoe", ABB group*) protoplasts isolated from regenerable embryogenetic cell suspensions." Plant Cell Reports, 13:262–266 (1994).

F.X. Cote, et al. "Embryogenic cell suspensions from the male flower of *Musa AAA cv. Grand nain*." Physiologia Plantarum 97:285–290 (1996).

A. Grapin, et al. "Somatic embryogenesis in plantain banana." In Vitro Cell Dev. Biol. Plant. 32:66–71 (1996).

G.D. May, et al. "Generation of transgenic banana (*Musa acuminata*) plants via *Agrovacterium*–mediated transformation." Biotechnology 13:486–492 (1995).

D. Dhed'a, et al. Plant regeneration in cell suspension cultures of the cooking banana cv. "Bluggoe" (*Musa* spp. ABB group). Fruits 46:125–135 (1991).

S. Sagi, et al. Genetic transformation of banana and plantain (*Musa* spp.) via particle bombardment. Biotechnology 13:481–485 (1995).

C.G. Marroquin, et al. Somatic embryogenesis and plant regeneration through cell suspensions in *Musa acuminata*. In Vivo Cell. Div. Biol. 29P:43–46 (1993).

J–V. Escalant, et al. Amplified somatic embryogenesis from male flowers of triploid banana and plantain cultivars (*Musa* spp.). In Vivo Cell Dev. Biol. 30P:181–186 (1994).

Ma, S.S., Somatic embryogenesis and plant regeneration from cell suspension culture of banana. Proceedings of symposium on tissue culture of horicultural crops. Taipei, Taiwan Mar. 8–9, 1988. Published by Department of Horticulture, National Taiwan University. Jun. 1991: 181–188.

*Primary Examiner*—Phuong T. Bui
*Attorney, Agent, or Firm*—Townsend and Townsend and Crew LLP

[57] ABSTRACT

The present invention provides a method of producing a transformed banana plant (genus,Musa), in particular by tranforming embroygenic material, or the somatic embryos derived from a banana plant, through incubation with Agrobacterium cells carrying exogenous DNA sequence(s), and obtaining regenerated plants.

25 Claims, No Drawings

METHOD OF GENETICALLY TRANSFORMING BANANA PLANTS

BACKGROUND OF THE INVENTION

The present invention relates generally to plant tissue culture and methods for genetically altering cells of higher plants. More particularly, the present invention relates to methods for genetically transforming banana plants (genus Musa), and obtaining regenerated plants therefrom.

Banana, including dessert bananas, plantain and cooking bananas, is among the most important staple food crop in the developing world. In fact, the fruits are the staple food for approximately 400 million people. The production of bananas has recently been seriously threatened by pests and many fungal, bacterial and virus diseases. Traditional methods of genetic improvement, however, cannot be used easily to transfer missing resistance characteristics to bananas, given sterility and ploidy issues arising in the triploid species.

Since breeding for improved traits is difficult and time consuming in banana plants, a preferred method for creating new varieties of banana is genetic engineering. In fact, genetic improvement of banana plants is a key goal of the scientific community. Genetic engineering of banana plants involves, among other methodologies, techniques for the introduction of exogenous DNA into banana cells and the regeneration of said transformed cells into banana plants identical to the original plant except for the presence of the introduced DNA. These techniques for gene introduction are preferably efficient in all steps of the process, from DNA delivery into the plant cells to regeneration of intact plants from the transformed plant cells.

Techniques for the in vitro culture of banana plants, including methods for the regeneration of plants from banana tissue cultures, have been described previously. In fact, there are commercial banana micropropagation facilities in which banana tissue culture is routinely practiced. However, these standard micropropagation methods are not suitable as the basis for a gene introduction method because in general, they not are compatible with DNA delivery.

In general, plants can be regenerated from tissue culture by direct organogenesis, indirect organogenesis, or somatic embryogenesis. Methods have been described previously for regenerating banana plants via direct organogenesis and somatic embryogenesis.

One method reported for banana transformation involves direct organogenesis and the use of an Agrobacterium-mediated DNA delivery. Arntzen, *Biotechnology* (1995); WO 95/15678. Another method for banana transformation that has been described involves somatic embryogenesis and a biollistic DNA delivery. Sagi (1995). It is, however, particularly desirable to find new and efficient methods for producing transgenic Musa plants.

SUMMARY OF THE INVENTION

The present invention is directed to methods of producing transformed banana plants (genus Musa), in particular by transforming embryogenic material (i.e., embryogenic callus or embryogenic cell suspension) or somatic embryos derived therefrom through incubation (or cocultivation) with Agrobacterium cells carrying exogenous DNA sequence(s), and obtaining regenerated plants therefrom. The method of the invention comprises the culturing of source tissues to produce somatic embryo or pro-embryo structures which in turn are cultured to produce embryogenic material, e.g. embryogenic callus or embryogenic cell suspension. The embryogenic material may be directly transformed with Agrobacterium to produce transformed embryogenic material which is then cultured to produce transformed somatic embryos. The embryogenic material also may be first cultured to produce somatic embryos and then transformed with Agrobacterium, the result being transformed somatic embryos.

Agrobacterium transformation preferably includes introduction of a marker to permit selection or screening of transformed cells. Transformed somatic embryos may be cultured to multiply or increase the number of transformed somatic embryos. Subsequently, germination is carried out to produce mature plantlets which may be transferred to soil conditions.

In one embodiment of this invention, the method comprises: (a) culturing somatic banana plant tissue to obtain at least one somatic embryo or pro-embryo structure; (b) culturing the somatic embryo or pro-embryo structure to obtain embryogenic material; (c) culturing the embryogenic material to obtain somatic embryos; (d) genetically transforming the somatic embryos produced in step (c) by co-cultivating with Agrobacterium cells carrying exogenous DNA sequence(s), the DNA sequence(s) which typically includes a selectable marker gene as well as one or more genes of interest to be expressed; (e) multiplying the transformed somatic embryo culture to produce additional transformed somatic embryos; and (f) germinating the transformed somatic embryos to produce a mature plantlet capable of being transferred to soil conditions.

In another embodiment of this invention, the method comprises: (a) culturing somatic banana plant tissue to obtain at least one somatic embryo or pro-embryo structure; (b) culturing the somatic embryo or pro-embryo structure to obtain embryogenic material; (c) genetically transforming the embryogenic material by co-cultivating with Agrobacterium cells carrying exogenous DNA sequence(s), which typically includes a selectable marker gene as well as one or more genes of interest to be expressed; (d) culturing the transformed embryogenic material to obtain transformed somatic embryos; and (e) germinating the transformed somatic embryos to produce a mature plantlet capable of being transferred to soil conditions.

The combination of Agrobacterium-mediated DNA delivery with somatic embryogenesis regeneration method in accordance with the present invention provides a particularly useful technique for selectively breeding new banana plants in a predictable and expeditious manner. A variety of traits, including agronomic traits such as disease resistance, yield etc. and quality traits, such as sweetness, flavor, acidity, color, etc., may be stably introduced into banana using the methods of the invention.

DETAILED DESCRIPTION OF THE INVENTION

This invention is directed to methods of genetically transforming banana by transformation with Agrobacterium, in particular, by transforming embryogenic material, e.g., embryogenic callus or embryogenic cell suspensions, or the somatic embryo cultures derived therefrom, with Agrobacterium to selectively introduce exogenous DNA sequence(s) in order to obtain genetically altered banana cells, embryos and plants. The methods may involve use of somatic banana plant tissue, embryogenic material, somatic embryos, DNA sequence(s) to be introduced, Agrobacterium cells to carry DNA sequence(s) and mediate their transfer to banana cells (e.g., embryogenic callus or cell suspensions or somatic embryos derived therefrom), and culture media suitable for the various steps, including embryogenic callus induction, embryo proliferation, and embryo and plantlet regeneration, as described.

The following terms, as used in the specification and claims, are intended to have the following meanings:

Somatic Embryo

Structures similar to zygotic embryos which arise from somatic cells. Somatic embryos can germinate and form whole plants which become "clones" of the source plant. In other words, the whole plants that germinate from the somatic embryos have a genetic make-up that is identical to the source plants. A pro-embryo is a structure that will become a somatic embryo.

Embryogenic Material

Cells which are capable of becoming somatic embryos, such as embryogenic callus or embryogenic cell suspensions. These cells are usually produced by culture of different organs in vitro. Embryogenic material may contain organized structures (e.g. pro-embryos) which are capable of maturing into somatic embryos.

Embryogenic Callus

Undifferentiated cell mass capable of becoming somatic embryos which is produced usually by culture of different organs in vitro. Callus can be hard, soft, dispersible, compact, spongy, dry, watery, or etc.

Embryogenic Cell Suspension

Undifferentiated cells dispersed within a liquid medium which are capable of becoming somatic embryos. These undifferentiated cells usually are produced by culture of different organs in vitro.

Mature Somatic Embryo

A structure derived from embryogenic cells that resembles a zygotic embryo morphologically and developmentally, and that is capable of germinating into a plantlet with both root and shoot poles, when transferred to a suitable growth medium.

Nutrient Media

Media that typically comprises salts, a carbon source and vitamins at concentrations necessary to effect the maintenance of cultured plant cells.

Effective Amount

Amount of a given component necessary to effect the recited step.

Operably Linked

Describing a functional linkage between two nucleic acids, for example, the linkage between a promoter and a second sequence, wherein the promoter sequence initiates and mediates transcription of the DNA sequence corresponding to the second sequence, or the linkage between a sequence and a 3' untranslated region/polyadenylation signal, wherein primary transcripts are cleaved and polyadenylated. Generally, operably linked means that the nucleic acid sequences being linked are contiguous and, where necessary to join two protein coding regions, contiguous and in the same reading frame.

Age of Embryogenic Material

The age of the embryogenic material (typically measured in days) is the time since last subculture of cell culture. Thus, a culture that is "less than 10 days old" is one that has been subcultured less than 10 days previously.

The banana plant tissue for use with this invention may be obtained from any species of the banana plant genus, Musa, including dessert bananas (karyotype AAA), plantains (karyotype AAB) and cooking bananas (karyotype ABB). See *Bananas and Plantains,* Ed. S. Gowen, published by Chapman and Hall, 26 Boundry Row, London SE1 8HN, United Kingdom, reprinted 1996, First Edition 1995. Exemplary species include *Musa acuminata, Musa balbisiana, Musa paradisiaca* (*M. sapiensis*), and the like. Of particular interest are various cultivars of *Musa acuminata* AAA cvs, especially members of the Cavendish subgroup such as Grand Nain, Williams, and the like.

Any banana plant tissue, including mature and immature somatic plant tissue, can be used as a source or explant material in the present invention as long as it is capable of producing embryogenic material or somatic embryos. Suitable somatic plant tissue includes tissue from staminate (i.e., male flowers), pistolate (i.e., female flowers), perfect flowers, corm discs, flowering stems, bracts, and the like. Immature flowers and corm discs are the preferred somatic plant tissue sources.

A preferred source material is flowers, and in particular immature flowers. Immature flowers are arranged in "hands" within the male bud. These flower hands are comprised of approximately 10 to 12 individual flowers and are identified by their position within the male bud (the first flower hand is located at the most proximal end of the floral meristem). The preferred flower hands for use in the present invention are flower hand numbers 15 to 30; flower hand numbers 20 to 30 being still more preferred.

Immature flower hands of Musa can be isolated and cultured to develop embryogenic callus or cell suspensions as described in Escalant J. V. et al. (1994, In Vitro Cell Dev. Biol. Plant 30: 181–186); Grapin, A. et al. (1996, In Vitro Cell Dev Biol. Plant 32:66–71) and Cote F. X. et al. (1996, Physiologia Plantarum 97: 285–290), the disclosures of which are incorporated herein in their entirety by reference.

Alternatively, embryogenic material can be obtained by auxin treatment of multiplying bud clusters sometimes referred to as "scalps," which can be induced in vitro on slices of corm tissue by culturing on nutrient medium supplemented with appropriate cytokinins, as described in Dhed'a D, et al. (1991, Fruits vol 46 number 2: 125–135), the disclosure of which is incorporated herein in its entirety by reference. Pro-embryo cultures developed on corm slices as described by Novak F. J. et al. (1989, Bio/Technology Vol 7: 154–159) can also be used with auxin treatment to obtain embryogenic material.

The exogenous DNA sequence(s) to be introduced will usually carry at least one selectable marker gene to permit screening and selection of transformed embryogenic material or the somatic embryos derived therefrom (i.e., those cells or embryos which have incorporated the exogenous DNA into their chromosomes), as well as one or more genes of interest which are chosen to provide, enhance, suppress, or otherwise modify expression of a desired trait or phenotype in the resulting plant. Such traits include agronomic traits such as disease resistance, yield, and the like, and quality traits, such as sweetness, flavor, acidity, color, and the like. Specific genes of interest include: ACC synthase, ACC oxidase, R genes, plant hormone biosynthetic genes or response genes, invertase, sucrose synthase, sucrose phosphate synthase, phosphorylase, carotenoid biosynthetic genes, and anthocyanin biosynthetic genes.

As used herein, "gene of interest" includes any nucleic acid (e.g., a gene or gene fragment) that is either heterologous or native to banana. A "heterologous gene" is one that originates from a foreign species, or, if from the same species, is substantially modified from its original form. For example, a heterologous promoter operably linked to a coding sequence is one from a species different from that from which the structural gene was derived, or, if from the same species, one or both are substantially modified from their original form.

The gene of interest to be introduced may be a structural gene which encodes a polypeptide which imparts the desired phenotype. Alternatively, the gene of interest may be a regulatory gene which may play a role in transcriptional and/or translational control to suppress, enhance, or otherwise modify the transcription and/or expression of an endogenous gene within the banana plant. It will be appreciated that control of gene expression can have a direct impact on the observable plant characteristics.

A number of DNA constructs can be used in a number of techniques to suppress expression of endogenous plant genes, e.g., sense or antisense suppression or ribozymes. Anti-sense RNA inhibition of gene expression has been shown; see, e.g., Sheehy et al., *Proc. Nat. Acad. Sci. USA*, 85:8805–8809 (1988), and Hiatt et al., U.S. Pat. No. 4,801, 340. The use of sense DNA sequences to suppress gene expression is described in various references, including Napoli et al. (1990 Plant Cell, 2:279–289 and U.S. Pat. No. 5,283,184, the disclosures of which are incorporated herein in their entirety by reference.

Often the nucleic acids to be introduced will be modified from their native form. For example, sense and anti-sense constructs referred to above often have all or a portion of the transcript of the native gene operably linked to a promoter sequence at the 5' end of the transcribable segment, and operably linked to another gene's 3' sequence (including polyadenylation sequences) at the 3' end of the transcribable segment. As is apparent to those skilled in the art, the promoter sequence could be one of the many plant active sequences. Alternatively, other plant-active promoter sequences could be derived specifically to be linked to the transcribable segment. The promoter may be endogenous to banana, or be from an exogenous source such as a cauliflower mosaic virus 35S promoter (Odell et al., Nature 313:810–812 (1985)). Promoters of choice are Ubi 1 of maize (Christensen et al., Plant Mol. Biol., 18, 675–89 (1992); and Synthetic Super MAS promoter (Ni et al., The Plant Journal, 7, 661–76 (1995).

Structural and regulatory genes to be inserted may be obtained from depositories, such as the American Type Culture Collection, Rockville, Md. 20852, as well as by isolation from other organisms, typically by the screening of genomic or cDNA libraries using conventional hybridization techniques, such as those described in Maniatis et al., *Molecular Cloning—A Laboratory Manual*, Cold Spring Harbor Laboratory, Cold Spring Harbor, N.Y. (1985). Screening may be performed by (1) nucleic acid hybridization using homologous genes from other organisms, (2) probes synthetically produced to hybridize to particular sequences coding for desired protein sequences, or (3) DNA sequencing and comparison to known sequences. Sequences for specific genes may be found in various computer databases, including GenBank, National Institutes of Health, as well as the database maintained by the Untied States Patent Office.

The genes of interest may also be identified by antibody screening of expression libraries with antibodies made against homologous proteins to identify genes encoding for homologous functions. Transposon tagging can also be used to aid the isolation of a desired gene. Transposon tagging typically involves mutation of the target gene. A mutant gene is isolated in which a transposon has inserted into the target gene and altered the resulting phenotype. Using a probe for the transposon, the mutated gene can be isolated. Then using the DNA adjacent to the transposon in the isolated, mutated gene, the normal wild-type allele of the target gene can be isolated. Such techniques are taught, for example, in McLaughlin and Walbot (1987) Genetics, 117:771–776; Dooner et al. (1985) Mol. Gen. Genetics, 200:240–246; and Federoff et al. (1984) Proc. Natl. Acad. Sci. USA, 81:3825–3829, the disclosures of which are incorporated herein in their entirety by reference.

The selectable marker gene on the DNA sequences to be inserted will usually encode a function which permits the survival of transformed callus, cell suspensions or somatic embryos in a selective medium. Usually, the selectable marker gene will encode antibiotic resistance, particularly Geneticin® resistance, kanamycin resistance, hygromycin resistance, streptomycin resistance, or the like, and herbicide resistance, particularly chlorosulfuron resistance, a nutritional marker, or the like. The composition of a suitable selective medium is described hereinbelow.

In addition to the gene of interest and the selectable marker gene, the DNA sequences may also contain a reporter gene which facilitates screening of the transformed callus, cell suspensions or somatic embryos for the presence and expression of the exogenous DNA sequence(s). Exemplary reporter genes include β-glucuronidase, as described in more detail hereinafter.

The exogenous DNA sequence(s) are introduced to the embryogenic callus or cell suspensions or somatic embryos by incubation with Agrobacterium cells which carry the sequences to be transferred within a transfer DNA (T-DNA) region found on a suitable plasmid. Typically, a binary vector system may be used to introduce the DNA sequences according to the present invention. A first plasmid vector would carry the T-DNA sequence while a second plasmid vector would normally carry a virulence (vir) region, which is essential for the transfer of the T-DNA, but is not itself transferred. By incubating Agrobacterium cells carrying both plasmids with the embryogenic callus, cell suspensions or somatic embryos, transformation of the callus, cell suspensions or somatic embryos can be achieved. The T-DNA is typically modified to delete the tumor inducing onc genes present in the T-DNA of wild-type Agrobacterium tumour-inducing (Ti) plasmids. By inserting the DNA sequence to be transferred into the T-DNA region, introduction of the DNA sequences to the plant genome can be effected. Other plasmids, including modified (co-integrate) Ti plasmids may be utilized in conjunction with Agrobacterium for transferring the DNA sequences of the present invention to the embryogenic callus, cell suspensions or somatic embryos.

The construction of recombinant binary and Ti plasmids may be accomplished using conventional recombinant DNA techniques, such as those described in Maniatis et al., supra. Frequently, the plasmids will include additional selective marker genes which permit manipulation and construction of the plasmid in suitable hosts, typically *E coli*. Suitable selective marker genes include tetracycline resistance, kanamycin resistance, ampicillin resistance, and the like.

The genes within the DNA sequences are typically linked to appropriate transcriptional and translational control sequences which are suitable for the banana plant host. For example, the genes are typically situated at a distance from a promoter corresponding to the distance at which the promoter is normally effective in order to ensure transcriptional activity. Usually, a polyadenylation site and transcription termination sites are provided at the 3'-end of the gene coding sequence. Frequently, the necessary control functions can be obtained together with the structural gene when it is isolated from a target plant of other host. Such intact genes will usually include coding sequences, intron(s), a promoter, enhancers, and all other regulatory elements either upstream (5') or downstream (3') of the coding sequence.

Suitable Agrobacterium strains include *Agrobacterium tumefaciens* and *Agrobacterium rhizogenes*. While the wildtype *Agrobacterium rhizogenes* could be used, the *Agrobacterium tumefaciens* should be "disarmed," i.e., have its tumor-inducing activity removed, prior to use. Preferred *Agrobacterium tumefaciens* strains include LBA4404, as described by Hoekema et al. (1983) Nature, 303:179–180, EHA101 (Hood et al. (1986) J. Bacteriol., 168:1291–1301, EHA105 (Hood et al. (1993) Transgenic Research 2: 208–21).

After the Agrobacterium strain(s) carrying the desired exogenous DNA sequence(s) are prepared, they are usually cultured for a period of time prior to incubation with the banana embryogenic callus or cell suspensions or the somatic embryos derived therefrom. Initially, the Agrobacterium may be cultured on a solid media including nutrients, an energy source, and a gelling agent. Suitable nutrients include salts, tryptone, and yeast extracts, while most sugars are suitable as the energy source and the gelling agent can be agar, Gel-rite®, or the like. A preferred medium is L-Broth or MinA media. Usually, medium will include an antibiotic to select for Agrobacterium carrying the plasmid DNA sequences.

Embryogenic material and the somatic embryos derived therefrom, which are generated from banana somatic plant tissue and which are targets for transformation by Agrobacterium, are preferably produced as follows: First, the banana somatic tissue is cultured on an initiation medium for approximately two to four months to obtain somatic embryo or pro-embryo structures. Preferred initiation media include M1 and modified MS1 medium, both of which are listed below in Table 1. Acceptable ranges and alternative components of M1 are listed below in Table 2. Second, these somatic embryo or pro-embryo structures are cultured in a proliferation medium for approximately four to six months to induce the development and increase the quantities of embryogenic material. Preferred proliferation media include M2 and ZZ, both of which are listed below in Table 1. Acceptable ranges and alternative components of M2 are listed below in Table 2. Third, in one embodiment, the embryogenic material is cultured in a regeneration medium for approximately one month to obtain somatic embryos therefrom. Preferred regeneration media include M3, which is listed below in Table 1. Acceptable ranges and alternative components of M3 are listed below in Table 2. Fourth, as explained below, somatic embryos may be cultured in a germination medium to produce plantlets. A preferred germination medium (M4) is listed below in Table 1. Acceptable ranges and alternative components for M4 are listed below in Table 2.

Agrobacterium transformation may take place after the somatic embryo or pro-embryo structures are obtained from the culturing on initiation medium, after the embryogenic material is obtained from the culturing on proliferation medium or after the somatic embryos are obtained from the culturing on regeneration medium. However, as further explained below, it is preferred that the Agrobacterium transformation take place after either the proliferation medium stage or the regeneration medium stage.

The somatic embryos produced as just described can be repeatedly subcultured in order to provide for an increased number of transformed/untransformed embryos. The untransformed somatic embryos can be used directly as a source for transformation or may be subcultured prior to use as a starting material. Subculturing allows the continuing maintenance of the somatic embryos as a source of starting materials for the method of the present invention.

In order to achieve the desired transformation, the embryogenic material, or the somatic embryos derived therefrom, is incubated (or cocultivated) with the Agrobacterium cells carrying the exogenous DNA sequence to be transferred. The age of the embryogenic material (i.e., time since last subculture) is related to the efficiency of transformation. For optimum levels of transformation, cultures should be about less than ten days old, preferably about five to about ten days old, and more commonly about seven days old. Incubation is preferably achieved in a cocultivation medium which includes nutrients, an energy source, and an induction compound which is used to induce the virulence (vir) region of Agrobacterium to enhance transformation efficiency. The induction compound can be any phenolic compound which is known to induce such virulence, preferably being acetosyringone (AS) present at from about 10 to 600 M, preferably at about 100–300 M.

Embryogenic material, or the somatic embryos derived therefrom, is combined with the Agrobacterium cells in the cocultivation medium at a moderate temperature, typically in the range from about 20 to 28 C., preferably at about 25–27 C., from two to four days, usually from about two to three days. The medium is preferably kept in the dark, and the cocultivation continued until the Agrobacterium have grown sufficiently so that colonies are observable on the calli or embryos, either directly or through a microscope.

The Agrobacterium cells are initially present at a concentration from about $10^7$ to $10^9$ cells/ml, preferably at about $10^8$ cells/ml. Usually, a total of about 0.25 to 10 ml settled cell volume of callus material is used in a total culture volume of about 1 to 100 ml. Preferably, the callus cells or somatic embryos and Agrobacterium cells are placed on a filter paper matrix, such as Whatman #1, or glass microfibre filter, on the cocultivation medium during the cocultivation process.

After transformation is completed, the embryogenic material or the somatic embryos derived therefrom is preferably washed from the Agrobacterium cells with water or a culture medium containing nutrients, an energy source, growth regulators, and the like. The transformed calli or embryos are mixed with the wash medium, typically at a volume ratio of from about 1:3 to about 1:30 (transformed material:liquid), preferably at about 1:10 and centrifuged, preferably at 500 rpm for about 5 minutes. The resulting liquid fraction containing most of the bacteria is removed, while the denser fraction containing the calli or embryos is saved. The wash is repeated, typically from two to six times, with antibiotics being used in at least the later washes in order to kill any remaining Agrobacterium cells. Any antibiotic capable of killing Agrobacterium may be used, with carbenicillin (200–1000 mg/l) being preferred.

After washing, the transformed embryogenic material or somatic embryos are placed on a suitable selection medium including a plant selection agent which permits identification of transformed calli or embryos based on the presence of the marker introduced as part of the exogenous DNA. Conveniently, the selective media is placed in a petri dish with portions of the calli, typically about 100–200 mg each. The selection medium is a general growth medium, such as the proliferation medium or ZZ medium, both of which are described in the Experimental section hereinafter, supplemented with the selection agent, and usually including the anti-Agrobacterium antibiotic. Suitable plant selection agents include Geneticin® (1–50 mg/l), chlorosulfuron (0.001–0.05 mg/l), kanamycin (100–500 mg/l), etc.

The selection culture is maintained typically for a time sufficient to permit transformed callus cells or somatic embryos to grow and produce white-cream colored calli, while the non-transformed callus cells and embryos turn brown and die. Typically, the selection culture will last from about 25 to 50 days, depending on the concentration and relative activity of the plant selective agent. The primary criterion in ending the selection culture, however, is a clear distinction between proliferating cells which have been transformed and non-proliferating cells which have not been transformed.

While viability is indicative that the embryogenic material (or the somatic embryos derived therefrom) have been transformed, it is usually desirable to confirm transformation using a standard assay procedure, such as Southern blotting, Northern blotting, restriction enzyme digestion, polymerase chain reaction (PCR) assays, or through the use of reporter genes. Suitable reporter genes and assays include -glucuronidase (GUS) assays as described by Jefferson, *GUS Gene Fusion Systems User's Manual*, Cambridge, England (1987) and luciferase assays as described by Ow (1986) Science 234:856–859. It will be appreciated that these assays can be performed immediately following the transformation procedures or at any subsequent point during the regeneration of the transformed plant materials according to the present invention.

Preferably, the transformed embryogenic material or the somatic embryos derived therefrom are then placed on a regeneration medium that includes plant selection agents in order to produce fully transformed somatic embryos. The regeneration medium is a general growth medium, such as the one which is described in the Experimental section hereinafter, supplemented with the selection agents, and usually including the anti-Agrobacterium antibiotic. Suitable plant selection agents include Geneticin® (1–50 mg/l), chlorsulfuron (0.001–0.05 mg/l), kanamycin (100–500 mg/l), etc.

The transformed embryogenic material or the somatic embryos derived therefrom are maintained for a time sufficient to permit transformed embryogenic material or somatic embryos to produce fully transformed somatic embryos. Typically, this "regeneration" from callus cells to somatic embryos (or multiplication of somatic embryos) will last from about 20 to 30 days.

Selection is also possible at the germination stage where transformed embryos germinate successfully on germination medium supplemented with a selective agent, while untransformed embryos do not. Early stages of embryo germination are characterized by hypocotyl elongation, cotyledonary leaf and chlorophyll development. In late stages of germination, cotyledonary leaf enlarges, the hypocotyl elongates, and a tap root develops. The differentiated embryos may be cultured on germination media, which is described in detail in the Experimental section hereinafter, for about 2 to 12 weeks. The result is somatic embryos with 10–20 mm in length having 2 to 4 leaves.

The germinated embryos are subsequently transferred to various media for further development into plantlets. Examples of the many suitable media for micropropagation of Musa have been published. Well developed plantlets can then be transferred to, for example, to the greenhouse or elsewhere in a conventional manner for tissue culture plantlets.

Transformation of the resulting plantlets can be confirmed by assaying the plant material for any of the phenotypes which have been introduced by the exogenous DNA. In particular, suitable assays exists for determining the presence of certain reporter genes, such as β-glucuronidase and/or luciferase, as described hereinabove. Other procedures, such as PCR, restriction enzyme digestion, Southern blot hybridization, and Northern blot hybridization may also be used.

The methods described above, and in the following examples, are applicable to a number of different Musa varieties, including "Grand Nain" and "Williams". The preferred choice of specific protocols may to some extent be genotype specific. Thus, one skilled in the art can readily adapt the present method to the various Musa varieties.

TABLE 1

MEDIA COMPOSITIONS

| | |
|---|---|
| Initiation Medium: | |
| M1: | MS salt mixture (1 X) |
| | MS vitamin mixture (1 X) |
| | L-glutamine (100 mg/l) |
| | Malt extract (100 mg/l) |
| | Sucrose (45.0 g/l) |
| | Biotin (1.0 mg/l) |
| | Gelrite (2.0 g/l) |
| | IAA (1.0 mg/l) |
| | NAA (1.0 mg/l) |
| | 2,4-D (4.0 mg/l) |
| | pH adjusted to 5.7 |
| Modified MS 1: | MS medium (4.4 g/l) |
| | Thiamine (0.4 mg/l) |
| | Ascorbic Acid (10.0 mg/l) |
| | 2,4-D (5.0 M) |
| | Zeatin (1.0 M) |
| | Macroelements and Iron (1/2 X) |
| Proliferation Medium: | |
| | MS salt mixture (1 X) |
| | MS vitamin mixture (1 X) |
| | L-glutamine (100 mg/l) |
| | Malt extract (100 mg/l) |
| | Sucrose (45.0 g/l) |
| | Biotin (1.0 mg/l) |
| | 2,4-D (1.0 mg/l) |
| | picloram (1.0 mg/l) |
| | auxin (0.5 to 5 mg/l when 2,4-D and picloram are used) |
| | pH adjusted to 5.3 |
| ZZ: | MS medium (2.2 g/l) |
| | Sucrose (30 g/l) |
| | 2,4-D (1.0 mg/l) |
| | Zeatin (Trans-isomers) (1μM) |
| | For semi-solid media: gelrite (2.2 g/l) |
| Regeneration Medium: | |
| M3: | MS salt mixture (1 X) |
| | MS vitamin mixture (#X) |
| | L-glutamine (100 mg/l) |
| | Malt extract (100 mg/l) |
| | Sucrose (45.0 g/l) |
| | Maltose (10.5 g/l) |
| | L-Proline (230 mg/l) |
| | Zeatin (0.05 mg/l) |
| | Kinetin (0.1 mg/l) |
| | 2iP (0.15 mg/l) |
| | NAA (0.2 mg/l) |
| | Gelrite (2.0 g/l) |
| | cytokinin (0.2 to 2 mg/l when zeatin, kinetin and 2iP are used) |
| | pH adjusted to 5.3 |
| Germination Medium: | |
| M4: | SH salt mixture (1 X) |
| | MS vitamin mixture (1 X) |
| | Sucrose (30 g/l) |
| | BA (1 mg/l) |

TABLE 1-continued

MEDIA COMPOSITIONS

GA (0.5 mg/l)
gelrite (3.0 g/l)
pH adjusted to 6.0

TABLE 2

ACCEPTABLE RANGES OF MEDIA COMPONENTS

| M1: | MS salt mixture | 0.25 X to 1.5 X |
|---|---|---|
| | MS vitamin mixture | 0.25 X to 1.5 X |
| | L-glutamine | 0.0 to 300 mg/l |
| | Malt extract | 0.0 to 300 mg/l |
| | Sucrose | 10 to 60 g/l |
| | Biotin | 0.0 to 15 mg/l |
| | gelrite | 1.5 to 4 g/l |
| | IAA | 0.0 to 15 mg/l |
| | NAA | 0.0 to 10 mg/l |
| | 2,4-D | 2 to 10 mg/l |
| | pH | 4.8 to 6.8 |
| M2: | MS salt mixture | 0.25 X to 1.5 X |
| | MS vitamin mixture | 0.25 X to 1.5 X |
| | L-glutamine | 0.0 to 300 mg/l |
| | Malt extract | 0.0 to 300 mg/l |
| | Sucrose | 10 to 60 g/l |
| | Biotin | 0.0 to 15 mg/l |
| | auxin | 0.0 to 5 mg/l |
| | pH | 4.8 to 6.8 |
| M3: | MS salt mixture | 0.25 X to 1.5 X |
| | MS vitamin mixture | 0.25 X to 1.5 X |
| | L-glutamine | 0.0 to 300 mg/l |
| | Malt extract | 0.0 to 300 mg/l |
| | Sucrose | 10 to 60 g/l |
| | Maltose | 0.0 to 60 g/l |
| | L-Proline | 0.0 to 500 mg/l |
| | cytokinin | 0.0 to 5 mg/l |
| | gelrite | 1.5 to 4 g/l |
| | pH | 4.8 to 6.8 |
| M4: | SH salt mixture | 0.25 X to 1.5 X |
| | MS vitamin mixture | 0.25 X to 1.5 X |
| | Sucrose | 10 to 60 g/l |
| | BA | 0.25 to 2 mg/l |
| | GA | 0.0 to 10 mg/l |
| | gelrite | 1.5 to 4 g/l |
| | pH | 4.8 to 6.8 |

EXAMPLE 1

Grand Nain inflorescences ("buds") from fields located in Costa Rica were used as the starting material. The outer bracts and flower hands of the buds were removed and discarded until approximately the terminal 2 cm of the true stem with inflorescences and bracts remained. This part of the bud was surface sterilized by immersion into a solution of 20% bleach for 15 minutes, followed by two brief rinses in sterile, distilled water. The bracts and flowers on this remaining bud continued to be removed and discarded using sterile technique in a laminar air flow hood until the 30$^{th}$ flower hand (approximately) was exposed. From this point on, the bracts were discarded but, the hands of flowers were individually placed on M1 medium until the flower hands became too small to practically remove (i.e., approximately, the fifth flower hand). The flower hands were incubated in a plant culture room set to run at a constant 28 C. under cool white fluorescent lights with a 16 hour photo period.

Approximately four months later, microscopic examination revealed that the flower hand located at position 27 (i.e., the 27$^{th}$ flower hand) had formed a cluster of somatic embryos. These somatic embryos were removed from the explant and transferred to a 250 ml Erlenmeyer flask containing 25 ml of liquid M2 medium. The flask was shaken at 100 rpm in the plant culture room described above. The culture was supplemented weekly with fresh media for two months by withdrawing about half of the liquid covering the cells (but avoiding removal of the cells themselves) and replacing it with fresh M2 media. At the end of the two month period, the resultant embryogenic suspension culture (hereinafter "ESC1") was maintained and propagated in the same environment described above with media supplementation done every 2 weeks by dividing the liquid and cells into two equal portions and making up the volume to 25 ml with fresh M2 media in each.

Transformation of ESC1 was initiated by cocultivation with *Agrobacterium tumefaciens*. A strain of *Agrobacterium tumefaciens* E2103 (which is the strain EHA101 carrying the plasmid pNPTII2103) was grown in liquid MinA media. The culture was adjusted to an optical density of 0.1 (approximately 10$^8$ bacteria per ml) by adding liquid MinA, and then was supplemented with 20 M acetosyringone immediately prior to cocultivation. Five ml of this bacterial culture was used to replace the liquid covering 0.5 ml of packed ESC1 cells. This mixture of bacterial and plant cells was shaken for approximately five minutes, then allowed to settle for about three minutes, after which 2.5 ml of the bacterial supernatant was removed. The remaining bacterial suspension and ESC1 cells were distributed over four glass fiber filter disks. Once evenly distributed, the remaining free liquid (i.e., the bacterial suspension) was removed. These Agrobacterium-soaked disks with ESC1 cells on top were placed over solid M2 media supplemented with 100 M acetosyringone and incubated for three days at 24 C. in darkness.

Selection for transformed banana cells and counterselection against the Agrobacterium was done by transferring the filter disks to solid M2 media supplemented with 25 mg/l Geneticin® (for selection) and 500 mg/l carbenicillin (for counterselection). After one month of incubation at 27 C. in 16 hour photo periods, the cultures were removed from the filter disks and transferred onto M3 medium supplemented with the same concentrations of selective and counterselective agents as described above. Globular embryos (which appeared after approximately one month) were placed on solid M4 medium supplemented with the growth regulators, 1 mg/l BA, 0.5 mg/l gibberellic acid (GA$_3$), the selective and counterselective agents 500 mg/l carbenicillin, and 50 mg/l Geneticin®.

After approximately three weeks of incubation on M4 media, shoots appeared which demonstrated β-glucuronidase ("GUS") expression in newly emerged leaf from a germinated embryo. GUS was expressed in all tissues assayed indicating that the germinated embryo was fully transformed.

Fully transformed plants, as shown by GUS assay as above, were also produced in this experiment when selection (i.e., application of the Geneticin®), was delayed for 1 week following the cocultivation, and when 400 mg/l of Timenton was used as the counterselective agent in place of the carbenicillin.

EXAMPLE 2

Grain Nain embryogenic suspension culture (ESC1) produced and maintained as described in Example 1 was used as starting material.

Transformation of ESC1 was initiated by cocultivation with the *Agrobacterium tumefaciens* strain E1301 (which is EHA101 carrying the plasmid pALS1301). The term "ALS"

refers to acetolactate synthase, which when expressed, provides resistance to chlorosulfuron. Preparation of the inoculum and cocultivation was done essentially as described in Example 1.

Selection for transformed banana cells and counterselection against the Agrobacterium was done by transferring the cells onto solid M2 media supplemented with 25 µg/l chlorosulfuron (for selection) and 500 mg/l carbenicillin (for counterselection). Following one month of incubation in 27 C., 16 hour photo periods, the cultures were transferred onto M3 media supplemented with 50 µg/l chlorosulfuron and 500 mg/l carbenicillin. Globular embryos, which appeared after approximately one month, were placed on solid M4 media supplemented with growth regulators (1 mg/l BA, 0.5 mg/l GA$_3$) and selective and counterselective agents (500 mg/l carbenicillin, 25 µg/l chlorosulfuron).

Shoots which appeared after four weeks of incubation on M4 media proved to be transformed as shown by GUS assay, as in Example 1.

Fully transformed plants, as shown by GUS assay as in Example 1, were also produced in this experiment when the following alterations of the above described conditions were applied: initial selection of 1 µg/l or 50 µg/l chlorosulfuron, application of the selective agent delayed for 4 weeks following the cocultivation, M2 media prepared with SH salts instead of MS salts and supplemented with 1 mg/l picloram instead of 2,4-D.

EXAMPLE 3

Regenerable Williams cell suspensions were developed from multiple-meristem budding cultures of Williams essentially according to the protocol described by Dhed'a D. et al. (1991) supra, with the following modification: the 'scalps' or meristematic bud clusters were produced using high cytokinin treatment (e.g., 5 to 10 mg/L BAP) of meristem tissues in the normal shoot tip culture medium. These scalps were then transferred to liquid ZZ medium.

These cultures were maintained in ZZ liquid medium with two-week subculture (1.5 ml PCV into 40 ml medium+10 ml conditioned medium). Cultures were optimized for fineness and rate of growth over many months. Suspensions were maintained on rotary shakers (90 rpm) at 25° C. (light conditions unimportant), with subculture every 2 weeks.

Cell suspensions in ZZ medium (preferably 7 days since last sub-culture) were prepared for transformation by filtering them through a 1 mm sieve. Liquid medium was removed from the filtrate and the remaining cells were washed with BMS medium. Cells (0.5 PCV aliquots in 2–3 ml BMS medium) were transferred to new tubes.

Binary vectors were transformed into Agrobacterium strains LBA4404 and EHA105 (Hood E. E. et al 1993, Transgenic Research 2: 208–218)) via direct, freeze-thaw transformation (Holsters M et al 1978, Mol. Gen. Genet. 163: 181–187) and subsequent selection. All GUS-based vectors have a plant intron spliced into the coding region of the GUS gene, to prevent expression in any residual Agrobacterium remaining after cocultivation and counterselection (Vancanneyt G et al 1990, Mol. Gen. Genet. 220: 245–250).

Glycerol stocks (kept at −70° C.) of Agrobacterium strains containing the desired binary vector were used to start overnight suspensions in LB+kanamycin (100 mg/l). Bacterial clumps were removed by centrifugation (30 seconds), then the suspensions were centrifuged (10 minutes) in order to pellet the remaining bacterial cells. The bacterial pellet was resuspended in 5 ml 1/2 MS medium+ acetosyringone (100 µM) and the bacterial density adjusted to between $10^7$–$10^8$ cells/ml.

Transformation of the Williams cell suspensions initiated by cocultivation with *Agrobacterium tumefaciens* strains LBA4404 and EHA105 containing plasmid pVGIN which contains GUS-intron and NPTII genes. Excess medium was removed from the Williams cultures and 3 ml of bacterial suspension added. These were left to incubate (with occasional inversion) for 30 minutes. Cells were then transferred onto 4.5 cm sterile filter discs (Whatman #1) and excess medium was blotted off. Filter discs were transferred individually to plates containing solid ZZ medium+100 µM acetosyringone. Cocultivation took place in a darkened 25° C. incubator for 48–72 hours. Filters were then transferred onto solid ZZ medium+500 mg/l carbenicillin to stop bacterial growth.

Selection for transformed banana cells and counterselection against the Agrobacterium was done by transferring the cocultivated cultures into liquid ZZ medium containing 100 mg/l kanamycin+500 mg/l carbenicillin for 3–4 weeks. Cultures were then transferred into liquid ZZ+10 mg/l Geneticin sulphate (G-418)+500 mg/l carbenicillin for full selection of stably transformed tissues. Transformed cell clusters appeared from 3–5 weeks after transfer to media containing Geneticin. The transformed status of embryogenic cell clusters was confirmed by GUS Assay and PCR.

Stably transformed, rapidly growing cell clusters can then be transferred to a series of regeneration media as described by Dhed'a et al., along with other media transfer to promote full regeneration of plantlets via germination of somatic embryos and caulogenesis.

The foregoing description and examples are for the purpose of illustration only and do not limit the scope of protection which should be accorded this invention. The disclosure of publications, patents and references cited above are incorporated herein in their entirety.

What is claimed is:

1. A method of producing a transformed banana plant comprising transforming banana embryogenic material from inflorescences with Agrobacterium containing a gene of interest and regenerating a transformed banana plant from the transformed embryogenic material.

2. The method of claim 1, wherein the embryogenic material is embryogenic callus from inflorescences.

3. The method of claim 1, wherein the embryogenic material is embryogenic cell suspension from inflorescences.

4. The method of claim 1, wherein the embryogenic material is less than ten days old since the last subculture.

5. The method of claim 1, wherein the Agrobacterium additionally contains a selectable marker gene.

6. The method of claim 5, wherein the selectable marker gene is selected from the group consisting of NPTII or ALS.

7. A method of producing a transformed banana plant comprising transforming a banana somatic embryo from inflorescences with Agrobacterium containing a gene of interest and regenerating a transformed banana plant from the transformed somatic embryo.

8. The method of claim 7, wherein the Agrobacterium additionally contains a selectable marker gene.

9. The method of claim 8, wherein the selectable marker gene is selected from the group consisting of NPTII or ALS.

10. The method of claim 7, further comprising the step of multiplying the transformed somatic embryo to produce additional transformed embryos after transforming the banana somatic embryo and before regenerating the transformed banana plant.

11. A method of genetically transforming banana, the method comprising:
   (a) culturing somatic banana plant tissue from inflorescences in a medium to obtain at least one somatic embryo structure or pro-embryo structure;
   (b) culturing the somatic embryo or pro-embryo structure in a medium to obtain embryogenic material;
   (c) transforming the embryogenic material with Agrobacterium cells having at least one exogenous DNA sequence to produce transformed embryogenic material;
   (d) culturing the transformed embryogenic material in a medium to produce at least one transformed somatic embryo; and
   (e) germinating the transformed somatic embryo in a medium to produce a mature plantlet capable of being transferred to soil conditions.

12. The method of claim 11, wherein the somatic embryo or pro-embryo structure of step (b) is cultured to obtain embryogenic callus.

13. The method of claim 11, wherein the somatic embryo or pro-embryo structure of step (b) is cultured to obtain embryogenic cell suspension.

14. The method of claim 11, wherein the Agrobacterium additionally contains a selectable marker gene.

15. The method of claim 14, wherein the selectable marker gene is selected from the group consisting of NPTII or ALS.

16. The method of claim 15, wherein the selectable marker gene is NPTII.

17. The method of claim 11, wherein the exogenous DNA sequence is a disease resistance gene.

18. The method of claim 11, further comprising the step of multiplying the transformed somatic embryo to produce additional transformed somatic embryos after step (d).

19. A method of genetically transforming banana, the method comprising:
   (a) culturing somatic banana plant tissue from inflorescences in a medium to obtain at least one somatic embryo structure or pro-embryo structure;
   (b) culturing the somatic embryo or pro-embryo structure in a medium to obtain embryogenic material;
   (c) culturing the embryogenic material in a medium to produce at least one somatic embryo;
   (d) transforming the somatic embryo produced in step (c) with Agrobacterium cells having at least one exogenous DNA sequence to produce transformed somatic embryos;
   (e) multiplying the transformed somatic embryo to produce additional transformed somatic embryos; and
   (f) germinating the transformed somatic embryo to produce a mature plantlet capable of being transferred to soil conditions.

20. The method of claim 19, wherein the somatic embryo or pro-embryo structure of step (b) is cultured to obtain embryogenic callus.

21. The method of claim 19, wherein the somatic embryo or pro-embryo structure of step (b) is cultured to obtain embryogenic cell suspension.

22. The method of claim 19, wherein the Agrobacterium additionally contains a selectable marker gene.

23. The method of claim 22, wherein the selectable marker gene is selected from the group consisting of NPTII or ALS.

24. The method of claim 23, wherein the selectable marker gene is NPTII.

25. The method of claim 19, wherein the exogenous DNA sequence is a disease resistance gene.

* * * * *